US00PP37784P2

(12) United States Plant Patent
Byrne et al.

(10) Patent No.: US PP37,784 P2
(45) Date of Patent: Oct. 20, 2026

(54) PEACH TREE NAMED 'TRH2E116L'

(50) Latin Name: *Prunus persica*
Varietal Denomination: TRH2E116L

(71) Applicant: The Texas A&M University System, College Station, TX (US)

(72) Inventors: David H. Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 15 days.

(21) Appl. No.: 19/336,383

(22) Filed: Sep. 22, 2025

(51) Int. Cl.
*A01H 5/08* (2018.01)

(52) U.S. Cl.
USPC ..... Plt./197

(58) Field of Classification Search
USPC ..... Plt./156, 180, 194, 197
See application file for complete search history.

(56) References Cited

U.S. PATENT DOCUMENTS

PP14,627 P3 3/2004 Byrne et al.
PP14,629 P3 3/2004 Byrne et al.
PP28,077 P3 6/2017 Byrne et al.

OTHER PUBLICATIONS

U.S. Appl. No. 19/336,141, filed Sep. 22, 2025, Byrne et al.
U.S. Appl. No. 19/336,148, filed Sep. 22, 2025, Byrne et al.
U.S. Appl. No. 19/336,164, filed Sep. 22, 2025, Byrne et al.
U.S. Appl. No. 19/336,169, filed Sep. 22, 2025, Byrne et al.
U.S. Appl. No. 19/336,358, filed Sep. 22, 2025, Byrne et al.
U.S. Appl. No. 19/336,361, filed Sep. 22, 2025, Byrne et al.
U.S. Appl. No. 19/336,363, filed Sep. 22, 2025, Byrne et al.
U.S. Appl. No. 19/336,365, filed Sep. 22, 2025, Byrne et al.
U.S. Appl. No. 19/336,368, filed Sep. 22, 2025, Byrne et al.
U.S. Appl. No. 19/336,370, filed Sep. 22, 2025, Byrne et al.
U.S. Appl. No. 19/336,372, filed Sep. 22, 2025, Byrne et al.
U.S. Appl. No. 19/336,375, filed Sep. 22, 2025, Byrne et al.
U.S. Appl. No. 19/336,377, filed Sep. 22, 2025, Byrne et al.
U.S. Appl. No. 19/336,380, filed Sep. 22, 2025, Byrne et al.
U.S. Appl. No. 19/336,385, filed Sep. 22, 2025, Byrne et al.
Rouse and Sherman. 1989. 'TropicBeauty': A low-chilling peach for subtropical climates. HortSci. 24(1): 165-166.

*Primary Examiner* — Karen M Redden
(74) *Attorney, Agent, or Firm* — Dentons US LLP

(57) ABSTRACT

Disclosed is a new variety of *Prunus persica* named 'TRH2E16L'. This new variety, which requires approximately 400 chilling units of dormancy, is a peach tree of early mid-season maturity, which produces yellow-fleshed, subacid, semi-freestone fruit that are very firm, with a 70-80% red blush over a yellow ground color, and suitable for the fresh market.

5 Drawing Sheets

Latin name of the genus and species of the plant claimed: *Prunus persica.*

Variety denomination: 'TRH2E116L'.

CROSS-REFERENCE TO RELATED APPLICATIONS

Peach trees developed under the same breeding program as 'TRH2E116L' include the co-pending applications listed below.

| U.S. application Ser. No. | Title |
|---|---|
| U.S. 19/295,148 | PEACH TREE NAMED 'TRH2E122W' |
| U.S. 19/336,141 | PEACH TREE NAMED 'TX3C490LWP' |
| U.S. 19/336,148 | PEACH TREE NAMED 'TRH2E68L' |
| U.S. 19/336,164 | PEACH TREE NAMED 'TRH3B53L' |
| U.S. 19/336,169 | PEACH TREE NAMED 'TRH3C114W' |
| U.S. 19/336,358 | PEACH TREE NAMED 'TRH2E121L' |
| U.S. 19/336,361 | PEACH TREE NAMED 'TRH3A17' |
| U.S. 19/336,363 | PEACH TREE NAMED 'TRH2E120LW' |
| U.S. 19/336,365 | PEACH TREE NAMED 'TRH3C113LW' |
| U.S. 19/336,370 | PEACH TREE NAMED 'TX2B449LW' |
| U.S. 19/336,372 | PEACH TREE NAMED 'TX2C465CW' |
| U.S. 19/336,375 | PEACH TREE NAMED 'TRH1C104LW' |

-continued

| U.S. application Ser. No. | Title |
|---|---|
| U.S. 19/336,377 | PEACH TREE NAMED 'TRH3C111' |
| U.S. 19/336,380 | PEACH TREE NAMED 'TRH2C108W' |
| U.S. 19/336,385 | PEACH TREE NAMED 'TRH2B102LW' |
| U.S. 19/336,368 | PEACH TREE NAMED TRH3E88LW' |

BACKGROUND OF THE INVENTION

This invention relates to peach trees and, more specifically, to peach trees referred to as a variety of *Prunus persica* named 'TRH2E116L', which requires approximately 400 chilling units of dormancy, produces firm, semi freestone subacid, yellow-fleshed peach with a 70-80% red blush over a yellow ground color that matures in the early mid-season. The present peach tree was the result of an ongoing Stone Fruit Breeding Program at College Station, Brazos County, Texas. To this end, controlled crosses are made each year to produce seedling populations from which improved progenies are evaluated and selected. The seedling 'TRH2E116L' was derived from a cross between low chill, subacid, white-fleshed nectarine 'Smooth Delight One' (patented, U.S. Plant Pat. No. 28,077) and a low-chill, yellow-flesh, acid, peach selection 'TX2B136' (not patented). 'TX2B136' was a seedling selected from a cross between the low chill cultivar 'Hermosillo' (not patented, Sherman, W. B., J. Rodriguez-Alcazar, and B. L. Topp. 1992. Peaches and nectarines developed but not introduced by the University of Florida. Fruit Varieties Journal 46:124-127) and the low chill peach selection 'TXW1293-1' (not patented). 'TXW1293-1' was a yellow-flesh, acid, low-chill peach selection made from a large open pollinated population of seedlings from 'Tropic Beauty' (not patented, Rouse, R. E. and W. B. Sherman. 1989. 'TropicBeauty': A low-chilling peach for subtropical climates. HortSci. 24(1): 165-166) as a female parent. The seed from the cross between 'Smooth Delight One' and 'TX2B136' were embryo cultured and planted in 2011 in an experimental plot in Floresville, TX. 'TRH2E116L' was marked for subsequent observation and noted as having exceptional characteristics in 2013.

'TRH2E116L' was bud grafted onto virus-free 'Nemaguard' (not patented, The Brooks and Olmo Register of Fruit and Nut Varieties, 3rd Ed., American Society of Horticultural Science Press, Alexandria, VA, 1997) peach rootstock at the nursery site in Oakdale, CA. The variety was subsequently planted and evaluated as two-year and older trees in Pleasanton (2018-2023), Somerville (2016-2023) and Fairfield (2015-2019), Texas. This evaluation clearly demonstrated that the re-propagated trees were true to the characteristics of the original seedling in all observable aspects.

SUMMARY OF THE INVENTION

The TRH2E16L peach is characterized as noteworthy by producing firm, subacid, yellow-flesh peach fruit that ripens in the early mid-season that has a 70-80% red blush over a yellow ground color. In this regard, the present variety of peach tree bears fruit that are ripe for commercial harvesting and shipment in early June, when the fruit is grown in the medium chill zone of Texas. 'TRH2E116L' blooms with its female parent 'Smooth Delight One' (Byrne, D. H. and N. Anderson. 2014. Smooth Delight One and Two, medium chill subacid nectarines. HortScience, 49(12):1593-1594; patented, U.S. Plant Pat. No. 28,077, 6 Jun. 2017) and ~10 days after its pollen parent 'TX2B136' (not patented). It ripens ~21 days after its female parent 'Smooth Delight One' and ~30 days after the pollen parent 'TX2B136'. 'TRH2E116L' differs from its female white-fleshed, subacid nectarine parent as it is a yellow-flesh peach and differs from its yellow-fleshed, acid, peach pollen parent as it has subacid flesh.

'TRH2E116L' has showy versus non showy flowers, has reniform versus globose glands, blooms about 2 weeks earlier, has yellow rather than white flesh. and ripens about 4 weeks later than the medium chill, white-fleshed, subacid peach cultivar 'White Delight One' (not patented, US 2016/2016/0205833 P1, abandoned). 'TRH2E116L' has a showy flower versus a non showy flower, has reniform glands versus globose glands, blooms about 2 weeks earlier, has yellow rather than white flesh, and ripens at the same time as 'White Delight Two' (not patented, US 2016/0205832 P1, abandoned).

'TRH2E116L' has yellow rather than white flesh, blooms about 4 days later and ripens about 1 week later than its sister seedling 'TRH1C104LW' (U.S. Ser. No. 19/336,375). As compared to 'TRH2E121L' (U.S. Ser. No. 19/336,358) and 'TRH3C111' (U.S. Ser. No. 19/336,377), the two cultivars which are derived from the reciprocal cross of the same parentage ('TX2B136' x 'Smooth Delight One'), 'TRH2E116L' differs as it blooms about 5 days after 'TRH3C111' and 3 days before 'TRH2E121L', requires about 400 chill units to bloom and fruit properly whereas 'TRH3C111' requires 300 chill units and 'TRH2E212L' requires 450 chill units, it has a red blush overcolor whereas that blush of both 'TRH3C111' and 'TRH2E121L' have darker blushes with more colorations in the red-purple and grey-purple groups of The R.H.S. 2001 Color Chart. This new subacid, yellow-flesh peach exhibits potential to be commercialized in regions that have chilling accumulation that are relatively low.

BRIEF DESCRIPTION OF THE DRAWINGS

This new variety of peach tree is illustrated by the accompanying photographs of 5-year old plants grown in Pleasanton, Texas, as provided in FIGS. 1-5. These photographs show the plant's typical fruit, foliage, and flowers, and the colors shown are as true as can be reasonably obtained by conventional photographic procedures.

DETAILED BOTANICAL DESCRIPTION

Figure 1:
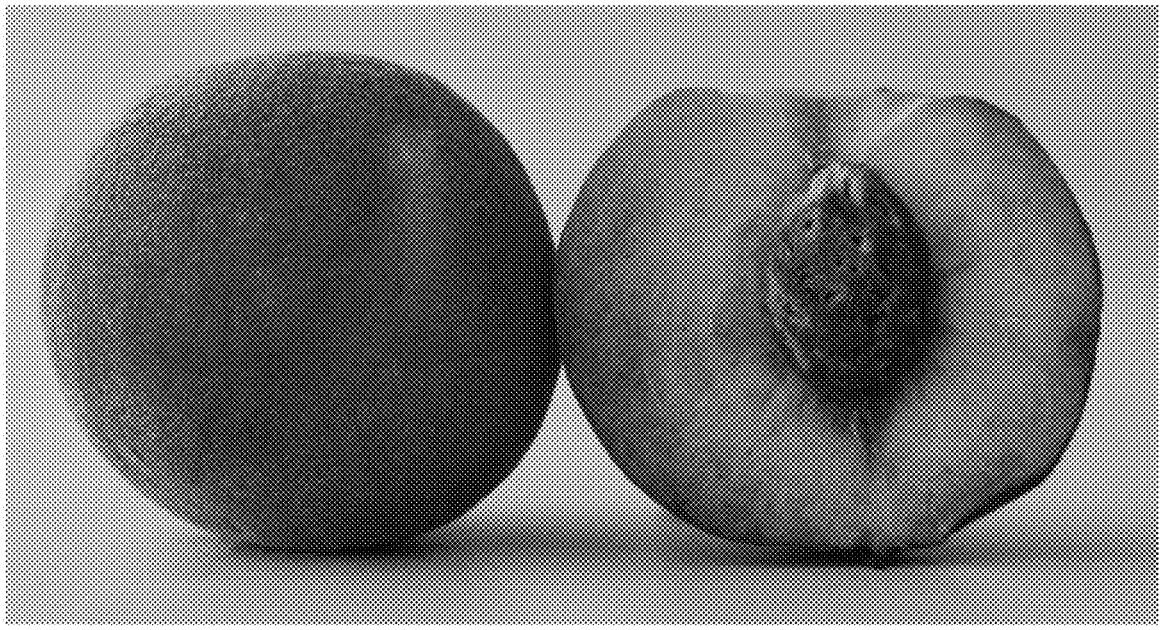
FIG. 1 Fruit of 'TRH2E116L' produced in Pleasanton, Texas showing external and internal coloration.
Figure 2:
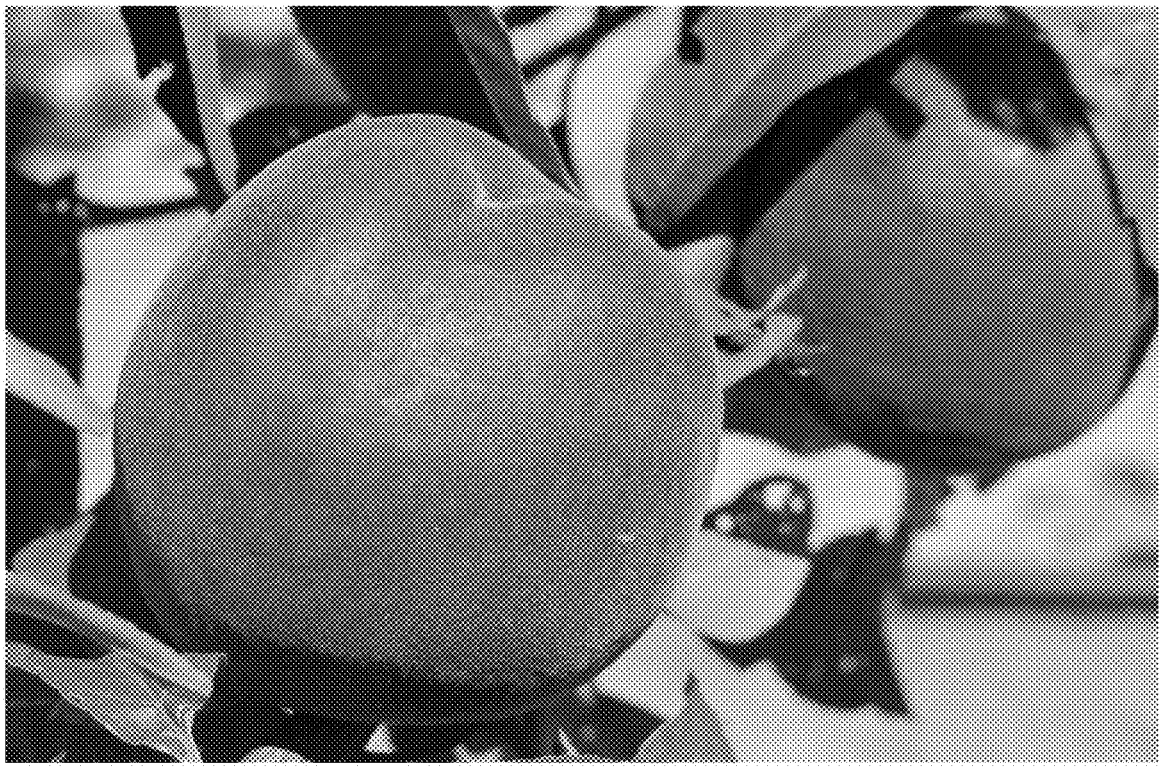
FIG. 2 'TRH2E116L' fruit produced in Pleasanton, Texas.
Figure 3:
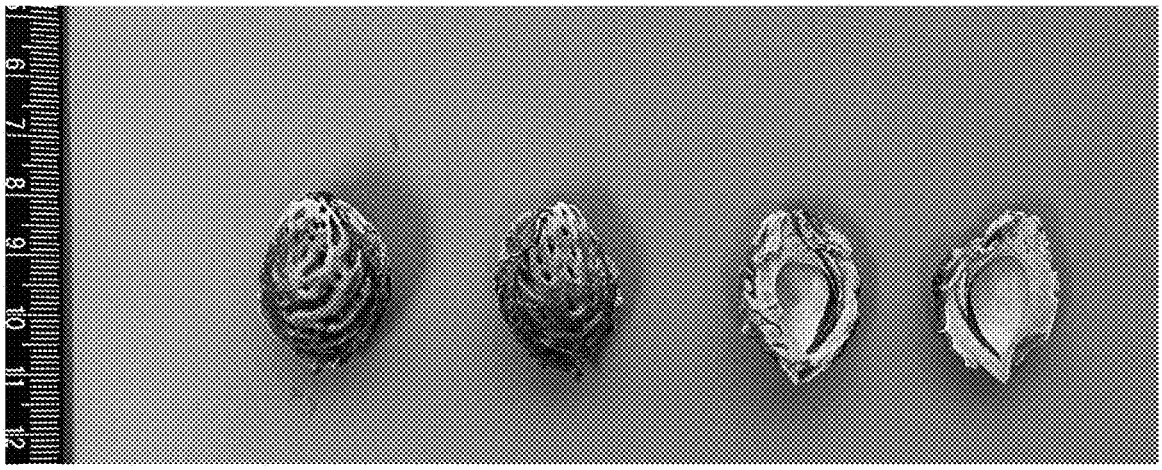
FIG. 3 Photograph of the endocarps of the 'TRH2E116L' peach. The ruler is in centimeters.
Figure 4:
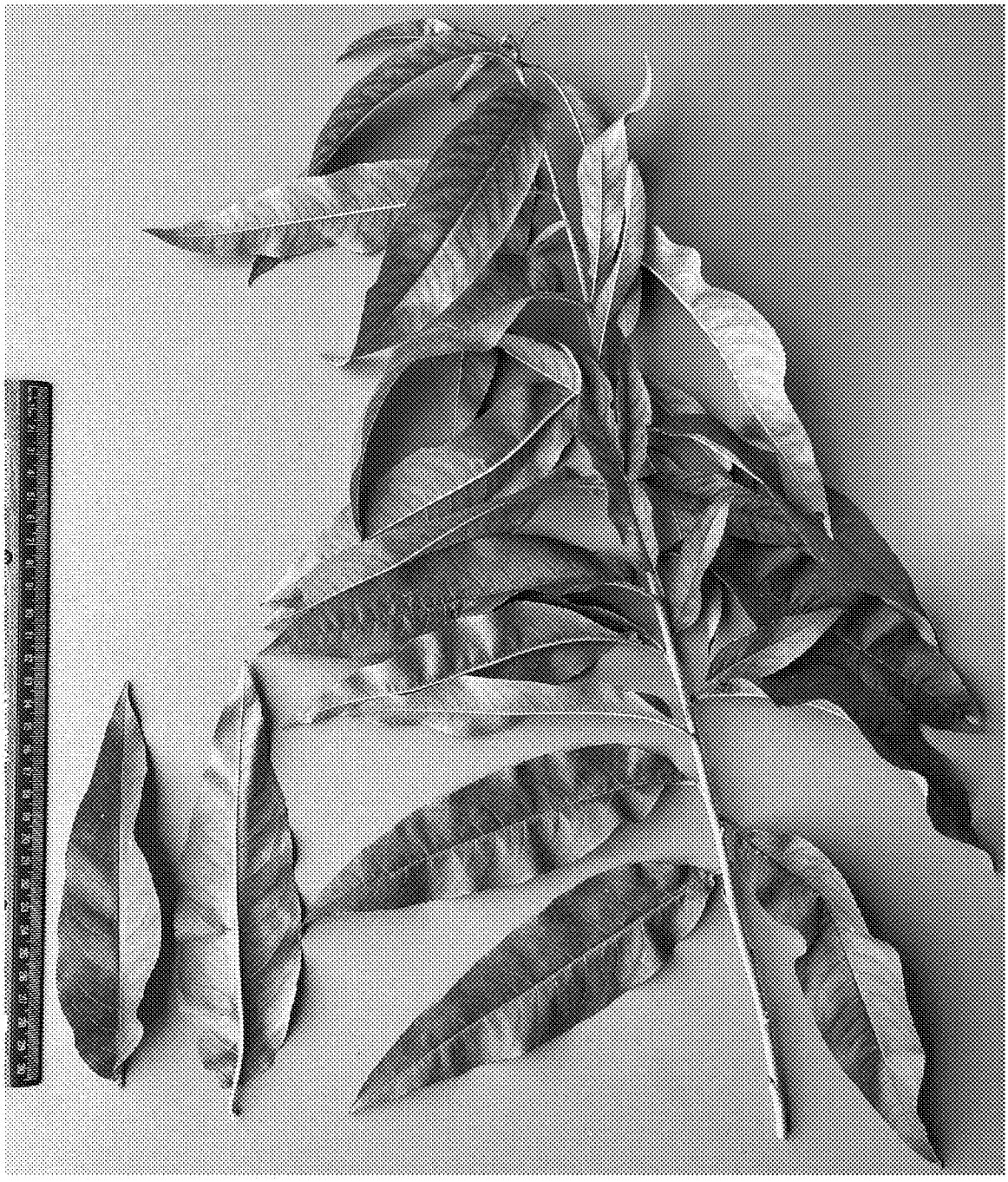
FIG. 4 A stem showing the leaves of the 'TRH2E116L' peach. The ruler is in centimeters.
Figure 5:
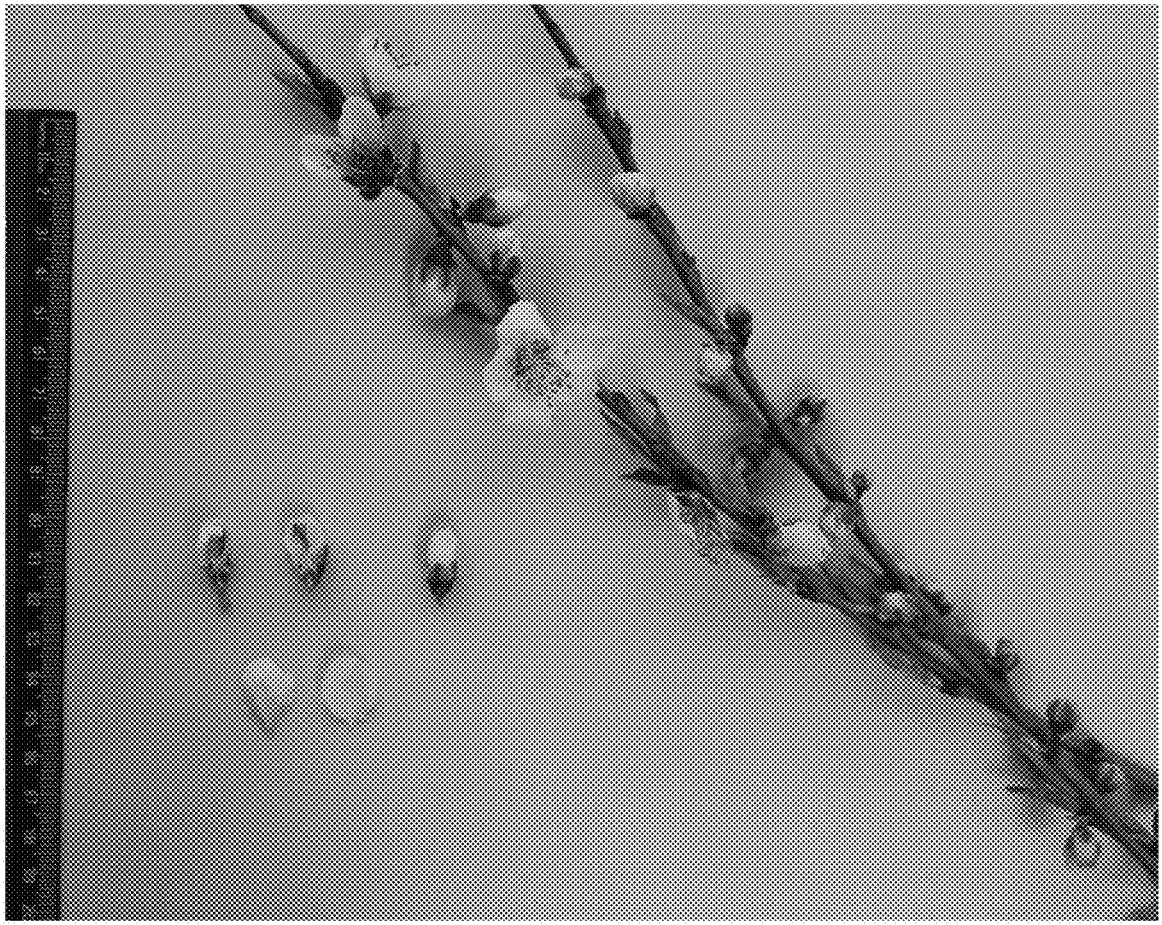
FIG. 5 A stem showing the flowers of the 'TRH2E116L' peach. The ruler is in centimeters.

Referring more specifically to the pomological details of this new and distinct variety of peach tree, the following has been observed under the ecological conditions prevailing at the experimental orchards in the medium chill zone of Texas (Pleasanton, Fairfield and Somerville). All major color code designations are by reference to The R.H.S. Colour Chart (2001 Edition) provided by The Royal Horticultural Society of Great Britain. Colors are approximate as color depends on horticultural practices such as light level and fertilization rate, among others.

Tree:

*Size*.—Generally average to above average as compared to other common peach cultivars grown in medium chill zone.

*Height*.—8 feet (2.4 m) at the end of the 2024 growing season.

*Width*.—7 feet width (2.1 m) at the end of the 2024 growing season.

*Productivity*.—Produces annually in the medium chill zone of Texas without alternate bearing if temperatures of 28° F. or lower are not experienced during bloom. Trees are self-fertile and must be fruit thinned most years to avoid limb breakage and obtain optimal fruit size. The recommended fruit spacing for early to mid-season ripening fresh market peach cultivars for a full crop is one fruit every 6-8" of one-year old fruiting wood. Trees often set more fruit than needed for a full crop.

*Shape*.—The 'TRH2E116L' peach has been trained in an open center configuration but exhibits a semi spreading growth type as seen in peach varieties 'Texprince' (patented, U.S. Plant Pat. No. 14,629) and 'Texking' (patented, U.S. Plant Pat. No. 14,627).

*Current season growth*.—The current season growth for the new variety was approximately 1 to 3.5 feet (0.3-1.1 m). Average vigor as compared to other commercial cultivars in the medium chill zone of Texas.

*Regularity of bearing*.—Regular in the absence of temperatures below 28° F. during bloom and considered hardy in the medium chill zone.

Trunk:

*Size*.—Approximately 2.5 inches (6.4 cm) in diameter and 8.25 inches (21 cm) in circumference when measured at a distance of approximately 12 inches (30.5 cm) above the soil level, at the end of the 2024 growing season on a three-year old tree.

*Bark texture*.—Considered moderately rough with numerous folds of papery scarf-like skin being present.

*Bark coloration* (*RHS*2001).—Variable, colors present are 156A, 156B, 156C, 156D of the Greyed-White Group, 163A, 163B, 164A, 164B, 164C, 165B, 167A, 175A, 175B and 176A of the Greyed-Orange Group and N200D of the Brown Group.

Branches:

*Thickness*.—Average to above average (about 4.5 cm in diameter as measured 10 cm from the trunk on a three-year old tree) as compared to other varieties.

*Surface texture*.—Average and appearing furrowed on wood that is several years old.

*Lenticels*.—Numerous flat, oval lenticels present. The lenticels range in size from approximately 5 to 8 mm in width and were approximately 2 mm in height.

*Current season shoots*.—Surface texture — Substantially glabrous.

*Internode length*.—Approximately 2.3 to 2.9 cm as measured in the middle of a current season stem.

*Color of mature branches* (*RHS*2001).—The predominant colors are 156C, 156D of the Greyed-White Group, 166B, 172A and 173A of the Greyed-Orange Group, N200D of the Brown Group and 201D of the Grey Group.

*Current season shoots*.—Color (RHS2001) — Light to medium green (146A, 146B, 146C of Yellow Group) with some reddish-brown coloration appearing on exposed surface of the shoots (166A of the Greyed-Orange Group and 178A, 178B of the Greyed-Red).

Leaves:

*Size*.—Considered moderately small for the species. Leaf measurements have been taken from vigorous upright current season growth approximately at mid-shoot.

*Leaf length*.—Approximately 117 to 136 mm.

*Leaf width*.—Approximately 33 to 40 mm.

*Leaf thickness*.—Less than 1 mm.

*Leaf form*.—Lanceolate.

*Leaf tip form*.—Acuminate.

*Leaf upper surface color* (*RHS*2001).—Green varying among 137A, 137B of the Green Group.

*Leaf lower surface color* (*RHS*2001).—Green varying among 146A, 146B of the Yellow-Green Group.

*Leaf lower mid-vein color* (*RHS*2001).—Light yellow green (145C and 154D of the Yellow-Green Group).

*Leaf margins*.—Form — Considered crenate. Uniformity — Considered generally uniform.

*Leaf petioles*.—Length — Approximately 6 to 9 mm. Thickness — Approximately 1.5 to 2 mm. Texture — Glabrous. Color (RHS2001) — Pale green (145A of the Yellow-Green Group).

*Leaf glands*.—Size — Approximately 1 mm in height and less than 1 mm in width. Number — Generally 0-2 per leaf. Type — Reniform. Color (RHS2001) — Brown (165A and 166A of the Greyed-Orange Group, N199B of the Greyed-Brown Group and 200B of the Brown Group).

*Leaf stipules*.—Length — Approximately 8 to 10 mm. Form — Lanceolate. Color (RHS2001) — Green (144B, 144C, N144A and 146D of the Yellow-Green Group). The stipules are early deciduous. Ratio of flower buds to vegetative buds — Generally 2 flower buds per vegetative bud.

Flowers:

*Floral buds*.—General — The floral buds are conic in form, and slightly appressed relative to the bearing shoot. Color — Dormant buds are light brown, (approximately 165A, 166A, 166B and 177A of the Greyed-Orange Group, 199B of the Grey-Brown Group and 200D of the Brown Group). Dormant Bud Length — Approximately 4 to 6 mm. Dormant Bud Width — Approximately 1 to 2 mm.

*Blooming type*.—Mean date of full bloom in the medium chill zone of Texas was in mid-February (February 14$^{th}$ at Somerville and February 18$^{th}$ at Fairfield experimental plot), a few days before or with the commercial cultivars 'Texking' and 'Flordaking' (Andrews, C. P. 1979. 'Flordaking' peach. HortScience 14(1):81-82).

*Flower type*.—Showy.

*Flower size*.—Flower diameter at full bloom is approximately 30 to 34 mm.

*Bloom quantity*.—Considered abundant.

*Flower bud frequency*.—Normally 1 to 2 per node.

*Petal size*.—Width — Approximately 10 to 14 mm. Length — Approximately 16 to 19 mm.

*Petal form*.—Broadly ovate.

*Petal number*.—Nearly always 5 per flower.

*Petal abaxial/adaxial color* (*RHS*2001).—Medium pink when young (56A of the Red Group; 62D, 65C, 65D, 69A, 69B, 69C and 73D of the Red-Purple Group and 75D of the Purple Group).

*Petal claw*.—Form — The claw is considered truncate in shape. Length — Approximately 1 mm. Width — Approximately 1 to 1.5 mm.

*Petal margins*.—Generally considered variable, from nearly smooth to slightly undulate.

*Petal apex*.—Generally — The petal apices appear rounded.

*Flower pedicel*.—Length — Average length of approximately 2 mm. Thickness — Approximately 1 mm. Color — A medium green (approximately 145A-B of the Yellow-Green Group).

*Floral nectaries*.—Color (RHS2001) — Dark orange (24A, 25A, 25B, N25A, N25B, 28A and 28B of the Orange Group and 30B, 30C and N30D of the Orange-Red Group).

*Sepals*.—

*Sepal number*.—Generally five per flower. Surface Texture — The surface has a short, fine, wooly and a white-colored texture. Size — Average Height 6.3 mm, Width 4.8 mm. Form — Ovate. Color (RHS2001) Maroon and medium green with a white (approximately 59B and 60A of the Red-Purple Group; 144B, 144C, N144C, N144D, 145A and 146D of the Yellow-Green Group; 155A, 155B, 155C, 155D of the White Group; 178A of the Greyed-Red Group and 183A, 183B, 183C and 185A of the Greyed-Purple Group).

*Floral cup* (*hypanthium*).—Surface Texture — Generally glabrous. Color (RHS2001) — Maroon with medium green (approximately 59B and 60A of the Red-Purple Group; 144B, 144C, N144C, N144D, 145A and 146D of the Yellow-Green Group; 178A of the Greyed-Red Group and 183A, 183B, 183C and 185A of the Greyed-Purple).

*Anthers*.—Color (RHS2001) — Dark red-orange (approximately 34A, 34B of the Orange-Red Group; 45A, 45B, 46A and 46B of the Red Group; 60A of the Red-Purple Group and 179A Greyed-Red Group).

*Pollen production*.—Pollen is abundant and is a medium to dark yellow color (RHS2001) (approximately 2A, 2B, 3A, 3B, 4A, 5A, 5B, 5C, 6A, 6B and 7A of the Yellow Group).

*Filaments*.—Size — Variable in length, approximately 10 to 15 mm, with the filaments slightly shorter or equal to the pistil and generally below the petal height at the pink bud stage. Color (RHS2001) — White (approximately 155A, 155B, 155C, 155D of the White Group) and darkening with advanced maturity.

*Pistil*.—General — Equal to or slightly taller to the general anther height and generally below the petal height at the pink bud stage. Length — Approximately 12 to 15 mm, including the ovary. Color (RHS2001) — Considered a light yellow-green when young (approximately 1B, 1C, 1D of the Green-Yellow Group and 2C, 2D, 4B, 4C and 4D of the Yellow Group), and becoming slightly darker with advancing senescence.

*Surface texture*.—The variety has a long, silver white pubescent pistil including the ovary (RHS2001) (approximately 155A, 155B, 155C, 155D of the White Group).

Fruit:

*Maturity when described*.—The present variety of fruit is described, as it would be found in its firm ripe condition at full commercial maturity. Under the ecological conditions prevailing in the medium chill zone of Texas it would be ripe in late May to early June. The average ripe date at Pleasanton, Somerville and Fairfield was May 21$^{st}$, June 4$^{th}$ and June 6$^{th}$ respectively.

*Size*.—General — Large for the season and considered uniform. Average Cheek Diameter — Approximately 60 to 66 mm. Average Suture Diameter — Approximately 61 to 67 mm. Average Axial Diameter — Approximately 56 to 58 mm.

*Fruit form*.—Generally considered round-ovate. Occasionally the fruit exhibits less symmetry when comparing the suture height with the line opposite the suture. The fruit is generally uniform in symmetry when viewed from the apical aspect.

*Fruit suture*.—Generally, the suture appears as a thin line that extends from the base to the apex, and appears deeper at the apex, forming a shallow basin at the apical point. No apparent callusing or stitching exists along the suture line. Fruit suture depth at the midpoint is less than 1 mm. Color (RHS2001) — The suture is dark red. Red Groups 46A and 53A, Red-Purple Group 59A, 59B and Greyed-Purple Groups 183A, 183B, 187A and 187B.

*Ventral surface*.—Form-Considered uniform.

*Stem cavity*.—Width — Approximately 15 to 19 mm. Length — Approximately 25 to 29 mm. Depth — Approximately 7 to 9 mm. Form — Considered variable from round to flat.

*Fruit base*.—Generally considered flat.

*Fruit apex*.—Generally considered flat.

*Fruit stem*.—Length — Approximately 9 to 10 mm. Thickness — Approximately 2 to 3 mm. Color (RHS2001) — Light to medium green, from 144B, 144C, N144C, N144D, 145A and 145B of the Yellow-Green Group.

*Fruit skin*.—Generally considered medium or average in thickness. Surface Texture — Light, short pubescence. Skin Acidity — Considered neutral. Tenacious to Flesh — Yes at commercial maturity. Tendency to Crack — Not observed. Skin Color — Generally-Variable, with solid red blush covering 70-80% of the fruit surface. Blush Color (RHS2001) — This red color (Orange-Red Group N34A and Red Groups 46A and 53A) exhibits many degrees of shading and blending between the stated colors. Skin Ground Color (RHS2001) — Generally considered from light to medium yellow (Yellow Groups 4D, 5D, 6D, 8C, 10C, 11C, 12D and 13D and Yellow-Orange Groups 14D, 15D and 16D).

*Flesh color* (*RHS*2001).—Considered a medium yellow color (Yellow Group 13B, 13C, Yellow-Orange Group 14C, 15D, 16B, 16D, 17D and 18A. The intensity of anthocyanin in the flesh are generally weak to medium near the skin, weak centrally and weak to medium near the stone.

*Flesh fibers*.—Present throughout the flesh.

*Stone cavity color* (*RHS*2001).—Generally considered dark pink (Red Groups 46A and 53A, Orange-Red Group N34A and Red-Purple Groups 58A, 60A, 60B and 61A.

*Flesh texture*.—Generally, the flesh is considered firm at commercial maturity.

*Ripening*.—Generally the fruit of the present variety ripens evenly.

*Flavor*.—Considered very sweet (average Brix 14.2) with a rich, subacid flavor.

Stone:

*Attachment*.—Semi freestone at commercial maturity.

*Stone size*.—Length — Approximately 29 to 32 mm. Width — Approximately 21 to 23 mm. Thickness — Approximately 17 to 18 mm.

*Fibers*.—Generally a few medium length fibers are attached sporadically along the surface of the stone.

*Stone form*.—Generally the stone is considered to be ovate.

*Stone base*.—The stone base is medium to wide.

*Base angle*.—The base angle of the stone is variable, but most frequently is considered slightly oblique to the stone axis.

*Hilum*.—The hilum is approximately 4 to 6 mm long and less than 1 mm wide.

*Apex shape*.—The stone apex is considered wide.

*Stone shape*.—Considered variable, from ovoid to elongated.

*Stone surface*.—Surface Texture — Consists of single pits, rosettes of pits and chains of pits. Ridges — Numerous fine ridges are present basally and converge towards the base of the stone.

*Ventral edge*.—Considered variable, from none to medium.

*Dorsal edge*.—Shape — Grooved and having moderately rough edges.

*Stone color* (*RHS*2001).—The color of the fresh stone is dark brown with medium pink (Red-Purple Groups 58A, 58B, 59C and 61B, Greyed-Orange Groups 165A, 166A, 177A and 177B and Greyed-Brown Group N199B). The color of the dry stone is tan to light brown (158A, 158B of the Yellow-White Group, 161B, 161C, 161D of the Greyed-Yellow, 164A, 164B, 164C, 164D, 165B, 165C, 165D, 166D and N167A of the Greyed-Orange and N199D of the Grey-Brown Group). The color of the inside surface of the endocarp is primarily Greyed-Orange Group 165B and Greyed-Brown Group N199D.

*Tendency to split*.—Splitting was not observed.

*Kernel*.—The kernel fills the endocarp at harvest and measures approximately 7 mm in thickness, 10-11 mm in width, and 16-17 mm in length. When dried the shriveled kernels measure approximately 4-5 mm in thickness, 9-10 mm in width, and 16 mm in length. The colors (RHS2001) of the fresh kernel are Yellow-Orange Group 18A, 18B, Yellow-White Group 158B, Greyed-Orange Groups 164A and 165B and Greyed-Brown Group N199D.

*Use*.—The subject variety, 'TRH2E116L', produces firm, semi freestone subacid, yellow-fleshed peaches with a 70-80% red blush over a yellow ground color that matures early mid-season that are suitable for the fresh market.

*Keeping quality*.—Good. Retains firmness and flavor after 14 days of refrigeration at 3-5° C.

*Resistance to insects and disease*.—No atypical resistances/susceptibilities were noted under normal cultural practices to date.

*Shipping quality*.—Average. Fruit does not develop internal breakdown and retains good firmness and eating quality after 14 days of refrigeration at 3-5° C.

Although the new variety of peach tree possesses the described characteristics when grown under the ecological conditions prevailing in the medium chill zone of Texas in Pleasanton, Somerville and Fairfield, it will be understood that variations of the usual magnitude and characteristics incident to the changes in growing conditions, fertilization, pruning, and pest control are to be expected.

What is claimed is:

1. A new and distinct variety of peach tree named 'TRH2E116L', as illustrated and described herein.

* * * * *